United States Patent [19]
Allen

[11] Patent Number: 5,464,048
[45] Date of Patent: Nov. 7, 1995

[54] LIQUID DISPENSER BOTTLES WITH RESERVOIRS FOR DROPPERS

[76] Inventor: Edward Allen, 16950 Jasmine St., #176, Victorville, Calif. 92392-5713

[21] Appl. No.: 199,808

[22] Filed: Feb. 22, 1994

[51] Int. Cl.⁶ .................................................. B65D 47/18
[52] U.S. Cl. .................... 141/24; 141/20.5; 141/285; 141/309; 141/326; 604/295; 215/6; 215/DIG. 3
[58] Field of Search .............. 141/21–24, 20.5, 141/285, 309, 325, 326; 220/555; 215/6, DIG. 3; 222/420, 421, 584; 604/217, 298, 295; 401/119, 126, 129; D9/338, 447

[56] References Cited

U.S. PATENT DOCUMENTS

| | | | |
|---|---|---|---|
| 461,126 | 10/1891 | Collins | 222/584 |
| 1,870,780 | 8/1932 | Milburn | 141/24 X |
| 2,058,516 | 10/1936 | Schaaff | 141/24 |
| 2,094,539 | 9/1937 | Jewett | 222/584 |
| 2,124,771 | 7/1938 | Fish | 222/584 |
| 2,233,160 | 2/1941 | Eisen | 215/6 X |
| 2,772,704 | 12/1956 | McConnell et al. | 141/24 |
| 3,060,942 | 10/1962 | Finlay | 222/584 |

FOREIGN PATENT DOCUMENTS

| | | | |
|---|---|---|---|
| 0519131 | 12/1932 | Australia | 222/584 |
| 0013336 | 3/1904 | Norway | 222/584 |
| 0324585 | 1/1930 | United Kingdom | 141/24 |
| 0737905 | 10/1955 | United Kingdom | 222/584 |

*Primary Examiner*—J. Casimer Jacyna

[57] ABSTRACT

A liquid dispenser bottle with reservoirs for droppers comprising a bottle having cylindrical side walls with a flat circular bottom and an open cylindrical top, the top being formed with external screw threads. A dropper has a cylindrical cap with downwardly extending sidewalls with internal screw threads removably couplable with the exterior screw threads of the bottle, a squeeze ball operatively coupled to the cap thereabove, and a cylindrical tube therebelow terminating in a spherical end with an aperture at its lowermost point for receiving and dispensing liquid through the squeezing and releasing of the bulb, the lower end of the cylinder having a diameter less than fifty percent of the diameter of the open cylindrical top of the bottle to allow insertion of the tube into the bottle at a predetermined angle, the length of the tube being less than the length of the cylinder but greater than the distance to a reservoir. A reservoir is formed into the interior of a cylindrical side wall of the bottle, the reservoir having an open upper edge of a diameter greater than the diameter of the dropper tube and with a spherical lowermost surface essentially the same shape as that of the lowermost same as that of the exterior end of the dropper, the reservoir having an interior surface constituting less than half of a sphere.

4 Claims, 5 Drawing Sheets

LIQUID DISPENSER BOTTLES WITH RESERVOIRS FOR DROPPERS

BACKGROUND OF THE INVENTION

1. Field of the Invention

The present invention relates to liquid dispenser bottles with reservoirs for droppers and more particularly pertains to dispensing essentially all liquid from a bottle through a reservoir built in to accommodate a dropper.

2. Description of the Prior Art

The use of bottles for use with droppers is known in the prior art. More specifically, bottles for use with droppers heretofore devised and utilized for the purpose of dispensing the liquid contents from bottles with droppers are known to consist basically of familiar, expected, and obvious structural configurations, notwithstanding the myriad of designs encompassed by the crowded prior art which has been developed for the fulfillment of countless objectives and requirements.

The prior art discloses a large number of bottles for use with droppers. By way of example, U.S. Pat. No. 3,756,478 to Hooker discloses a dropper dispenser.

U.S. Pat. No. 3,756,478 to Podell discloses an eye drop dispenser with liquid metering device.

U.S. Pat. No. 4,286,633 to Herr discloses a dropper assembly.

U.S. Pat. No. 4,982,875 to Pozzi discloses a cap, reservoir and dropper assembly for bottles.

U.S. Pat. No. 5,154,702 to Foyil discloses a variable dosage dropper system.

In this respect, liquid dispenser bottles with reservoirs for droppers according to the present invention substantially depart from the conventional concepts and designs of the prior art, and in doing so provide an apparatus primarily developed for the purpose of dispensing essentially all liquid from a bottle through a reservoir built in to accommodate a dropper.

Therefore, it can be appreciated that there exists a continuing need for new and improved liquid dispenser bottles with reservoirs for droppers which can be used for dispensing essentially all liquid from a bottle through a reservoir built in to accommodate a dropper. In this regard, the present invention substantially fulfills this need.

SUMMARY OF THE INVENTION

In view of the foregoing disadvantages inherent in the known types of bottles for use with droppers now present in the prior art, the present invention provides improved liquid dispenser bottles with reservoirs for droppers. As such, the general purpose of the present invention, which will be described subsequently in greater detail, is to provide new and improved liquid dispenser bottles with reservoirs for droppers and methods which have all the advantages of the prior art and none of the disadvantages.

To attain this, the present invention essentially comprises a new and improved liquid dispenser bottle with a reservoir for droppers comprising, in combination, a bottle having cylindrical side walls with a flat circular bottom and an open cylindrical top, the top being formed with external screw threads. A dropper has a cylindrical cap with downwardly extending sidewalls with internal screw threads removably couplable with the exterior screw threads of the bottle, a squeeze ball operatively coupled to the cap thereabove, and a cylindrical tube therebelow terminating in a spherical end with an aperture at its lowermost point for receiving and dispensing liquid through the squeezing and releasing of the bulb, the lower end of the cylinder having a diameter less than fifty percent of the diameter of the open cylindrical top of the bottle to allow insertion of the tube into the bottle at a predetermined angle, the length of the tube being less than the length of the cylinder but greater than the distance to a reservoir. A reservoir is formed into the interior of a cylindrical side wall of the bottle, the reservoir having an open upper edge of a diameter greater than the diameter of the dropper tube and with a spherical lowermost surface essentially the same shape as that of the lowermost same as that of the exterior end of the dropper, the reservoir having an interior surface constituting less than half of a sphere. The reservoir is molded into the bottle with an indentation formed in the exterior side wall of the bottle at a location immediately beneath the reservoir. A plurality of air channels extend from the upper edge of the reservoir to a common point at the lowermost extent of the reservoir.

There has thus been outlined, rather broadly, the more important features of the invention in order that the detailed description thereof that follows may be better understood and in order that the present contribution to the art may be better appreciated. There are, of course, additional features of the invention that will be described hereinafter and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of descriptions and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

Further, the purpose of the foregoing abstract is to enable the U.S. Patent and Trademark Office and the public generally, and especially the scientists, engineers and practitioners in the art who are not familiar with patent of legal terms or phraseology, to determine quickly from a cursory inspection the nature and essence of the technical disclosure of the application. The abstract is neither intended to define the invention of the application, which is measured by the claims, nor is it intended to be limiting as to the scope of the invention in any way.

It is therefore an object of the present invention to provide new and improved liquid dispenser bottles with reservoirs for droppers which have all the advantages of the prior art bottles for use with droppers and none of the disadvantages.

It is another object of the present invention to provide new and improved liquid dispenser bottles with reservoirs for droppers which may be easily and efficiently manufactured and marketed.

It is a further object of the present invention to provide new and improved liquid dispenser bottles with reservoirs for droppers which are of a durable and reliable construction.

An even further object of the present invention is to provide new and improved liquid dispenser bottles with reservoirs for droppers which are susceptible of a low cost of manufacture with regard to both materials and labor, and which accordingly are then susceptible of low prices of sale to the consuming public, thereby making such liquid dispenser bottles with reservoirs for droppers economically available to the buying public.

Still yet another object of the present invention is to provide new and improved liquid dispenser bottles with reservoirs for droppers which provide in the apparatuses and methods of the prior art some of the advantages thereof, while simultaneously overcoming some of the disadvantages normally associated therewith.

Even still another object of the present invention is to dispense essentially all liquid from a bottle through a reservoir built in to accommodate a dropper.

Lastly, it is an object of the present invention to provide a new and improved liquid dispenser bottle with reservoirs for droppers comprising a bottle having cylindrical side walls with a flat circular bottom and an open cylindrical top, the top being formed with external screw threads. A dropper has a cylindrical cap with downwardly extending sidewalls with internal screw threads removably couplable with the exterior screw threads of the bottle, a squeeze ball operatively coupled to the cap thereabove, and a cylindrical tube therebelow terminating in a spherical end with an aperture at its lowermost point for receiving and dispensing liquid through the squeezing and releasing of the bulb, the lower end of the cylinder having a diameter less than fifty percent of the diameter of the open cylindrical top of the bottle to allow insertion of the tube into the bottle at a predetermined angle, the length of the tube being less than the length of the cylinder but greater than the distance to a reservoir. A reservoir is formed into the interior of a cylindrical side wall of the bottle, the reservoir having an open upper edge of a diameter greater than the diameter of the dropper tube and with a spherical lowermost surface essentially the same shape as that of the lowermost same as that of the exterior end of the dropper, the reservoir having an interior surface constituting less than half of a sphere.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be had to the accompanying drawings and descriptive matter in which there is illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein.

The same reference numerals refer to the same parts throughout the various Figures.

DESCRIPTION OF THE PREFERRED EMBODIMENT

Figure 1:
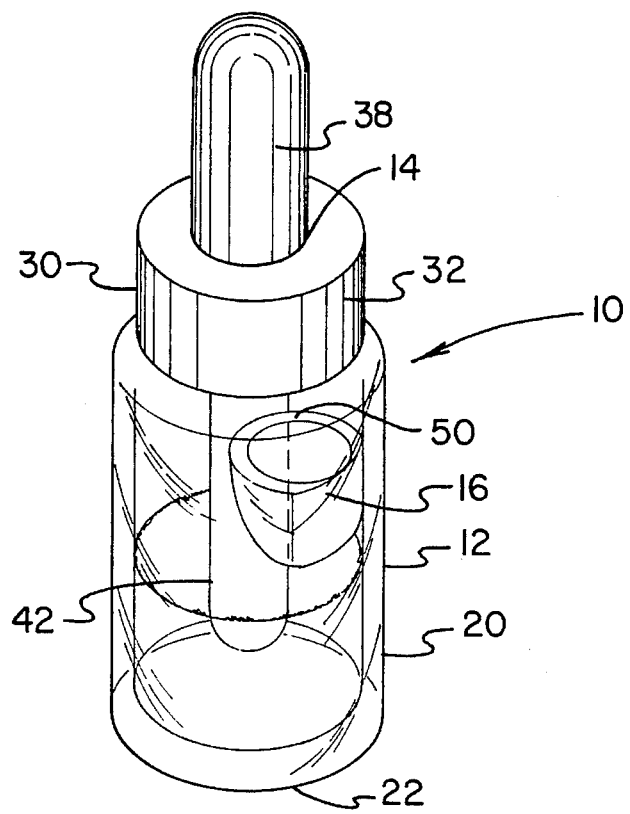
FIG. 1 is a perspective illustration of the preferred embodiment of the liquid dispenser bottles with reservoirs for droppers constructed in accordance with the principles of the present invention.
Figure 2:
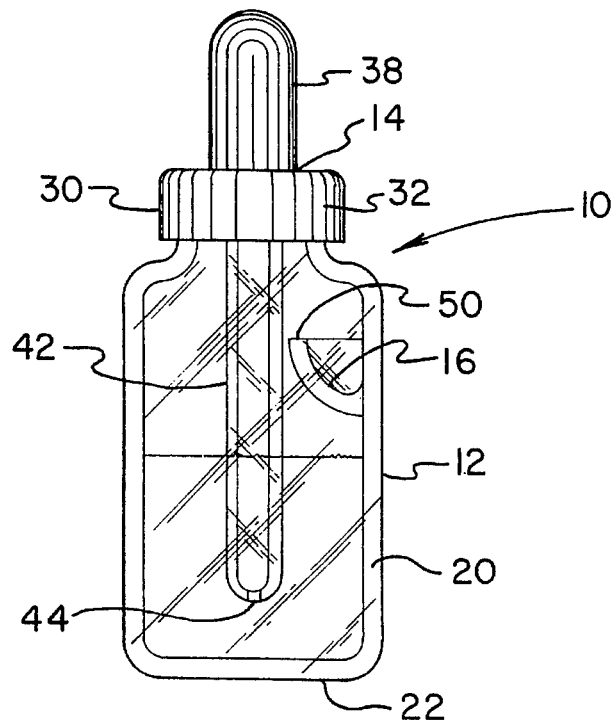
FIG. 2 is a front elevational view of the device shown in FIG. 1.
Figure 3:
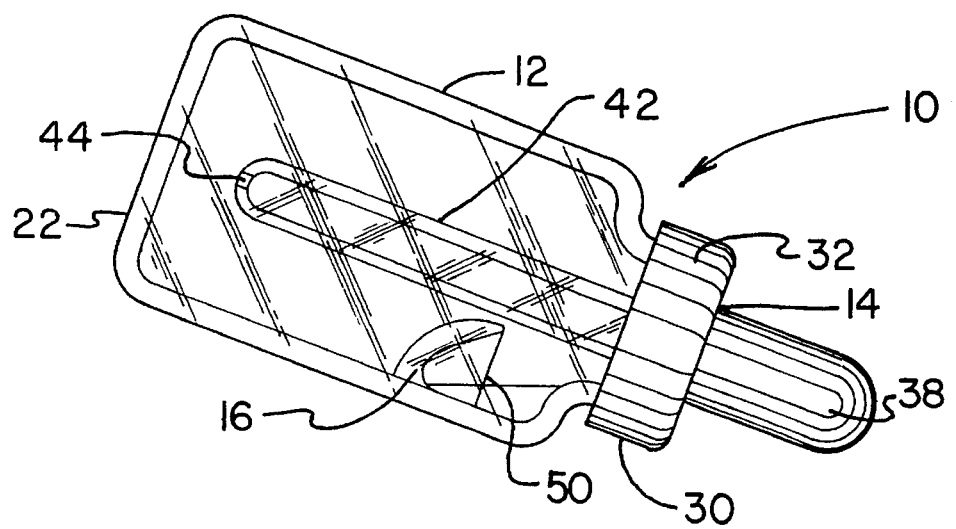
FIG. 3 is a front elevational view of the device shown in FIG. 1 but with the bottle tipped for filling the reservoir.
Figure 4:
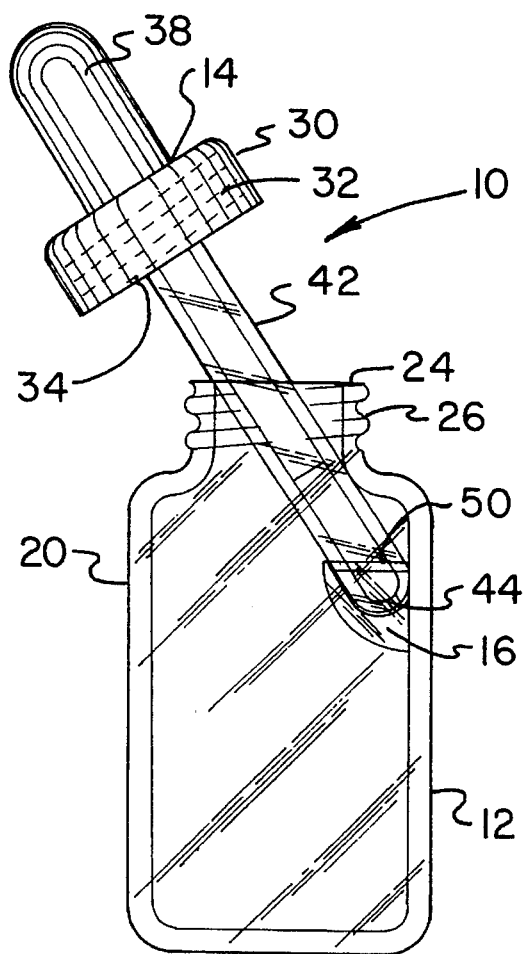
FIG. 4 is a front elevational view of the device shown in FIG. 1 and showing the dropper removing the contents from the reservoir.

With reference now to the drawings, and in particular to FIG. 1 thereof, the preferred embodiment of the new and improved liquid dispenser bottles with reservoirs for droppers embodying the principles and concepts of the present invention and generally designated by the reference numeral 10 will be described.

Specifically, it will be noted with reference to the FIGS. 1 through 4 there is shown the present invention which is a new and improved liquid dispenser bottle with reservoirs for droppers. In its broadest terms, the invention comprises a device 10 having a bottle 12, a dropper 14 and a reservoir 16.

More specifically, the bottle 12 has cylindrical side walls 20. Coupled to the side walls 20 is a flat bottom 22 in a circular configuration. An open cylindrical top 24 is at the upper end of the side walls 20. The top 24 is formed with external screw threads 26.

The second component of the device 10 is a dropper 14. The dropper has a cylindrical cap 30. The cap has downwardly extending sidewalls 32 with internal screw threads 34. Such screw threads 34 are removably couplable with the exterior screw threads 26 of the bottle. A squeeze ball 38 is operatively coupled to the cap 20 thereabove. A cylindrical tube 42 is provided therebelow as part of the dropper 14. The lowermost end of the tube 42 is hemispherical in shape and terminates in an aperture 44 at its lowermost end. The aperture 44 receives and dispenses liquid through the squeezing and release of the squeezeball 38. The lower end of the cylinder has a diameter less than fifty percent of the diameter of the opening at the top of the bottle. This allows insertion of the tube into the bottle at a predetermined angle for maximum removal of the liquid. Note FIG. 3. The length of the tube is less than the length of the cylindrical tube 42 but greater than the distance to the bottom of the reservoir 48.

The reservoir 16 is formed into the interior of the cylindrical wall of the bottle 12. The reservoir has an open upper edge 50 of a diameter slightly greater than the diameter of the dropper tube to allow entry of the tube at an angle. The reservoir 48 has a spherical surface similar in size and shape to the lower end of the dropper but slightly larger so that the exterior end of the dropper will contact the reservoir bottom for the sucking up of all liquid in the reservoir. The reservoir 16 has an interior surface constituting less than half of a sphere.

Figure 5:
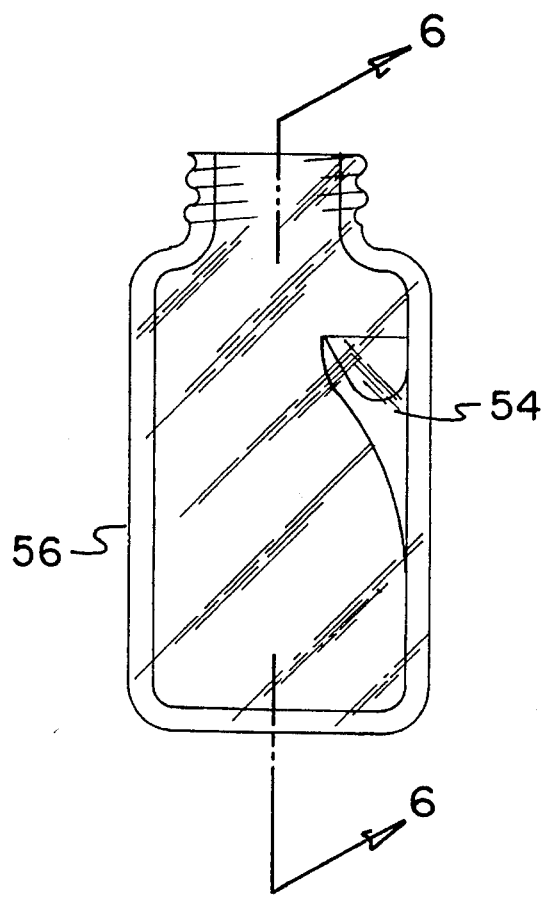
FIG. 5 is a front elevational view of a bottle constructed in accordance with an alternate embodiment of the invention.
Figure 6:
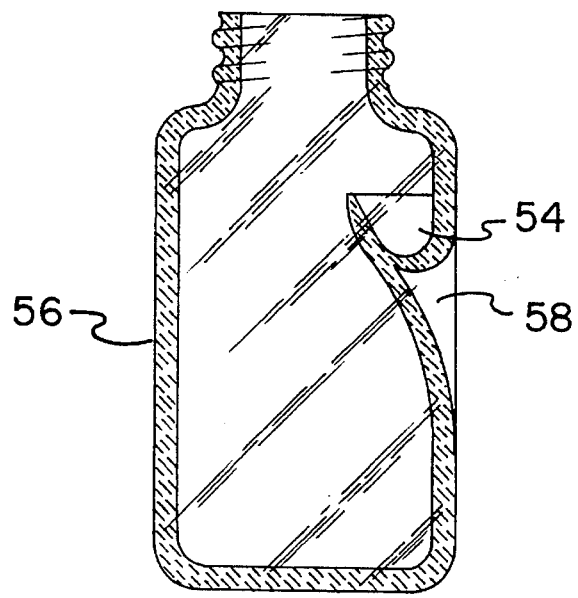
FIG. 6 is a sectional view taken along line 6—6 of FIG. 5.

FIGS. 5 and 6 illustrate an alternate embodiment of the invention. In such embodiment, the reservoir 54 is molded into the bottle 56. An indentation 58 is formed in the exterior side wall. Such indentation is located in the bottle at a location immediately beneath the reservoir. This allows use of the bottle in the dark since the reservoir is easily located.

Figure 7:
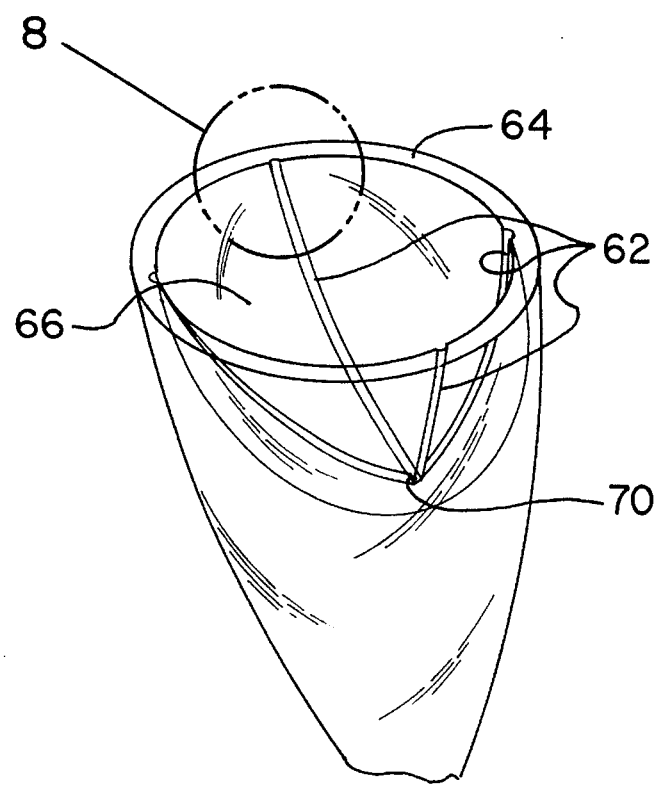
FIG. 7 is a perspective illustration of a reservoir constructed in accordance with an alternate embodiment of the invention.
Figure 8:
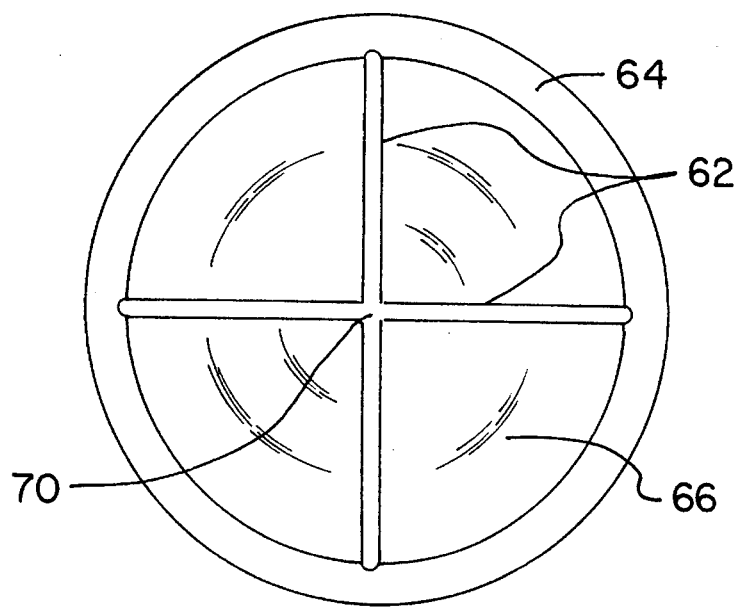
FIG. 8 is a top plan view of the reservoir shown in FIG. 7.
Figure 9:
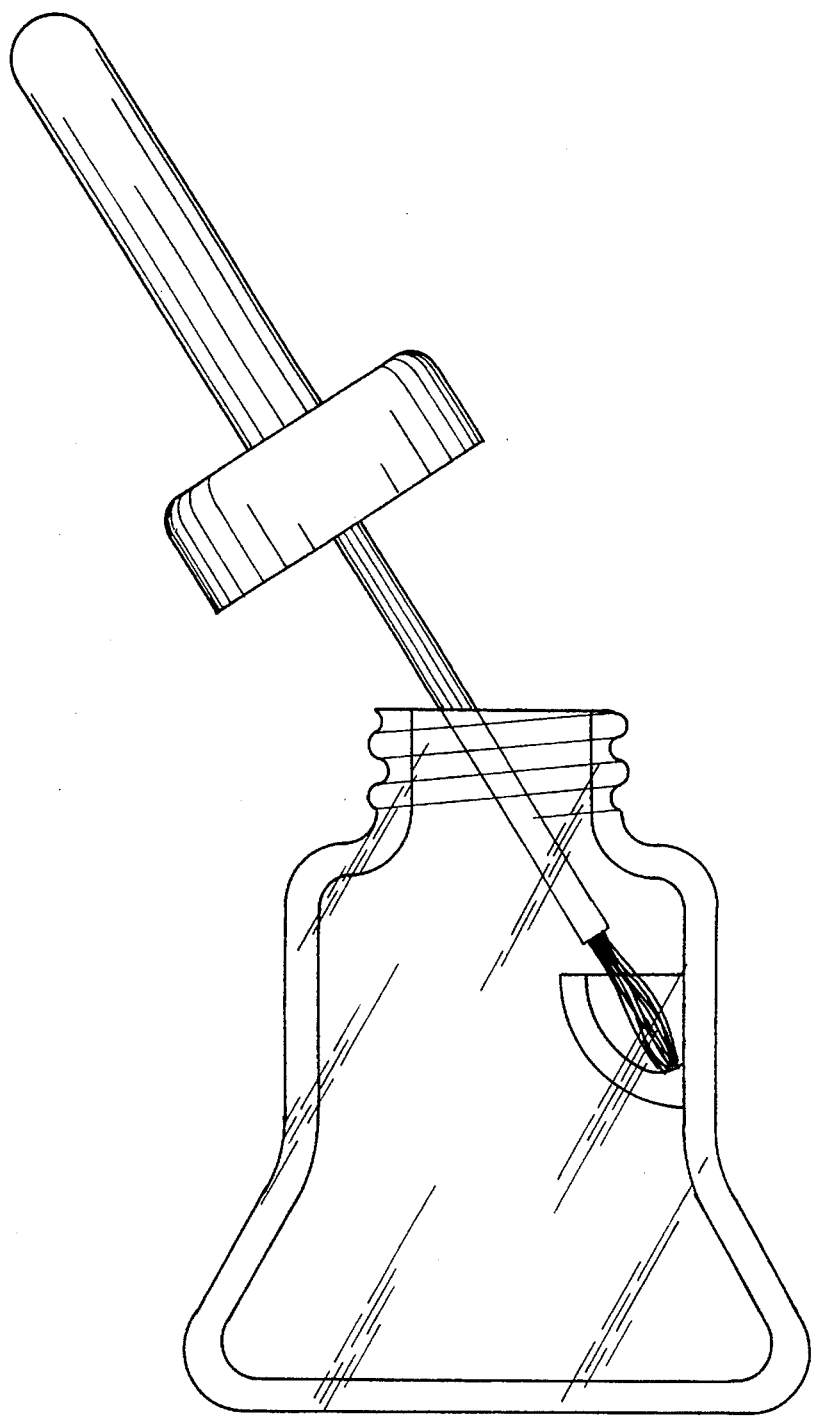
FIG. 9 is a side elevational view of an alternate embodiment of the invention shown during operation and use.

FIGS. 7 and 8 show another alternate embodiment of the invention. In such embodiment, a plurality of air channels 62 extend from the upper edge 64 of the reservoir to a common point 70 at the lowermost edge of the reservoir. This further insures that the liquid will flow to the bottom of the reservoir 66. This is further insurance that all liquid will be sucked up by the dropper 14.

The present invention solves a problem which is encountered by everyone. In some cases the problem is of little consequence, but in other instances, it is very annoying because of the costs involved. The problem occurs when trying to remove the entire contents from a container which utilizes a dropper to place the medications or other substances in a specific location, like the eyes, ears and nose. To allow the material to be drawn into it, the end of the tube on the dropper does not extend all the way down to the bottom of the bottle. This makes it impossible to withdraw the entire amount of the medication from the container. Since many medications are very expensive, and are sold in very small amounts such as one ounce or less, it is understandable that many people become irritated by such callous disregard of their money on the part of the company that has packaged the product.

The present invention is a container which makes it possible to retrieve virtually all of the solution it contains. This is accomplished by providing a small open reservoir near the top of the bottle. When the liquid level has dropped below the end of the dropper tube, the container is tilted to allow the material at the bottom to flow into the reservoir, where it can be retrieved with the dropper. The reservoir is molded directly into the plastic bottle. The present invention is also applicable to other compounds, such as nail polishes. This capability can be added at almost no additional cost, since the reservoir can be incorporated into the molding dies used to produce the bottles.

As to the manner of usage and operation of the present invention, the same should be apparent from the above description. Accordingly, no further discussion relating to the manner of usage and operation will be provided.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

What is claimed as being new and desired to be protected by Letters Patent of the United States is as follows:

1. A new and improved liquid dispenser bottle with a reservoir for droppers comprising, in combination:

a bottle having cylindrical side walls with a flat circular bottom and an open cylindrical top, the top being formed with external screw threads;

a dropper having a cylindrical cap with downwardly extending sidewalls with internal screw threads removably couplable with the exterior screw threads of the bottle, a squeeze ball operatively coupled to the cap thereabove, and a cylindrical tube therebelow terminating in a spherical end with an aperture at its lowermost point for receiving and dispensing liquid through the squeezing and releasing of the ball, the lower end of the cylinder having a diameter less than fifty percent of the diameter of the open cylindrical top of the bottle to allow insertion of the tube into the bottle at a predetermined angle;

a reservoir formed into the interior of a cylindrical side wall of the bottle, the reservoir having an open upper edge of a diameter greater than the diameter of the dropper tube and with a spherical lowermost surface essentially the same shape as that of the exterior end of the dropper, the reservoir having an interior surface constituting less than half of a sphere, the length of the tube being less than the length of the cylinder but less than the distance between the open cylindrical top of the bottle and the reservoir;

the reservoir being molded into the bottle with an indention formed in the exterior side wall of the bottle at a location immediately beneath the reservoir; and a plurality of air channels extending from the upper edge of the reservoir to a common point at the lowermost extent of the reservoir.

2. A liquid dispenser bottle with a reservoir for droppers comprising:

a bottle having cylindrical side walls with a flat circular bottom and an open cylindrical top, the top being formed with external screw threads;

a dropper having a cylindrical cap with downwardly extending linear sidewalls with internal screw threads removably couplable with the exterior screw threads of the bottle, a squeeze ball operatively coupled to the cap thereabove, and a cylindrical tube therebelow terminating in a spherical end with an aperture at its lowermost point for receiving and dispensing liquid through the squeezing and releasing of the ball, the lower end of the cylinder having a diameter less than fifty percent of the diameter of the open cylindrical top of the bottle to allow insertion of the tube into the bottle at a predetermined angle; and a reservoir formed into the interior of a cylindrical side wall of the bottle, the reservoir having an open upper edge of a diameter greater than the diameter of the dropper tube and with a spherical lowermost surface essentially the same shape as that of the exterior end of the dropper to retain fluid when the bottle is erect, the reservoir having an interior surface constituting less than half of a sphere, the length of the tube being less than the length of the cylinder but less than the distance between the open cylindrical top of the bottle and the reservoir.

3. The bottle as set forth in claim 2 wherein the reservoir is molded into the bottle with an indentation formed in the exterior side wall of the bottle at a location immediately beneath the reservoir.

4. The bottle as set forth in claim 2 and further including a plurality of air channels extending from the upper edge of the reservoir to a common point at the lowermost extent of the reservoir.

* * * * *